United States Patent [19]

Pusineri et al.

[11] Patent Number: 5,015,388
[45] Date of Patent: May 14, 1991

[54] INTEGRATED DEVICE FOR THE BIOSPECIFIC PURIFICATION OF A LIQUID CONTAINING CELLULAR ELEMENTS

[75] Inventors: Christian Pusineri, St Symphorien d'Ozon; Michel Cronenberger, Mornant, both of France

[73] Assignee: Hospal Industrie, Cedex, France

[21] Appl. No.: 327,621

[22] Filed: Mar. 24, 1989

[30] Foreign Application Priority Data

Mar. 25, 1988 [FR] France ................. 88 04234

[51] Int. Cl.$^5$ .............. B01D 61/14; B01D 61/18; B01D 63/02; B01D 63/08

[52] U.S. Cl. .................... 210/641; 210/645; 210/650; 210/660; 210/691; 210/790; 210/806; 210/314; 210/321.64; 210/321.83; 210/321.84; 210/321.85; 210/321.89; 210/434; 210/489; 210/492; 435/174; 435/182; 435/288; 435/311; 604/5; 604/6

[58] Field of Search .............. 210/645, 790, 806, 314, 210/315, 321.64, 621.83, 321.84, 321.85, 321.88, 321.89, 433.1, 434, 486, 487, 489, 492, 641, 650, 660, 691; 604/4, 5, 6; 435/174, 182, 817, 288, 311

[56] References Cited

U.S. PATENT DOCUMENTS

| | | | |
|---|---|---|---|
| 3,579,441 | 5/1971 | Brown | 210/434 |
| 3,827,565 | 8/1974 | Matsumura | 210/321.75 |
| 4,000,072 | 12/1976 | Sato et al. | 210/315 |
| 4,013,564 | 3/1977 | Nose | 210/434 |
| 4,127,481 | 11/1978 | Malchesky et al. | 210/434 |
| 4,243,532 | 1/1981 | Tsuda et al. | 210/434 |
| 4,361,484 | 11/1982 | Larsson et al. | 210/651 |
| 4,849,102 | 7/1989 | Latour et al. | 210/321.64 |
| 4,861,485 | 8/1989 | Fecondini | 210/314 |

FOREIGN PATENT DOCUMENTS

| | | |
|---|---|---|
| 139949 | 8/1984 | European Pat. Off. . |
| 2828549 | 6/1978 | Fed. Rep. of Germany . |
| 2758679 | 7/1979 | Fed. Rep. of Germany ............ 210/321.64 |
| 2035134 | 9/1969 | France . |
| 2325390 | 9/1976 | France . |
| 62-114606 | 5/1987 | Japan ............ 210/321.64 |
| 2040724A | 1/1980 | United Kingdom . |
| WO88/09693 | 12/1988 | World Int. Prop. O. ...... 210/321.64 |

Primary Examiner—W. Gary Jones
Attorney, Agent, or Firm—Finnegan, Henderson, Farabow, Garrett & Dunner

[57] ABSTRACT

A device for biospecifically purifying a liquid having a first portion containing cellular elements and a second portion without cellular elements, the device comprising a casing, a duct for conducting the liquid into the casing, a filter disposed within the casing for tangentially filtering the liquid to separate first portion from the second portion, a filter disposed within the casing for transversely filtering the separated second portion to biospecifically purify the liquid after the separation of the cellular elements, ducts for evacuating the first portion and second portion from the casing.

16 Claims, 12 Drawing Sheets

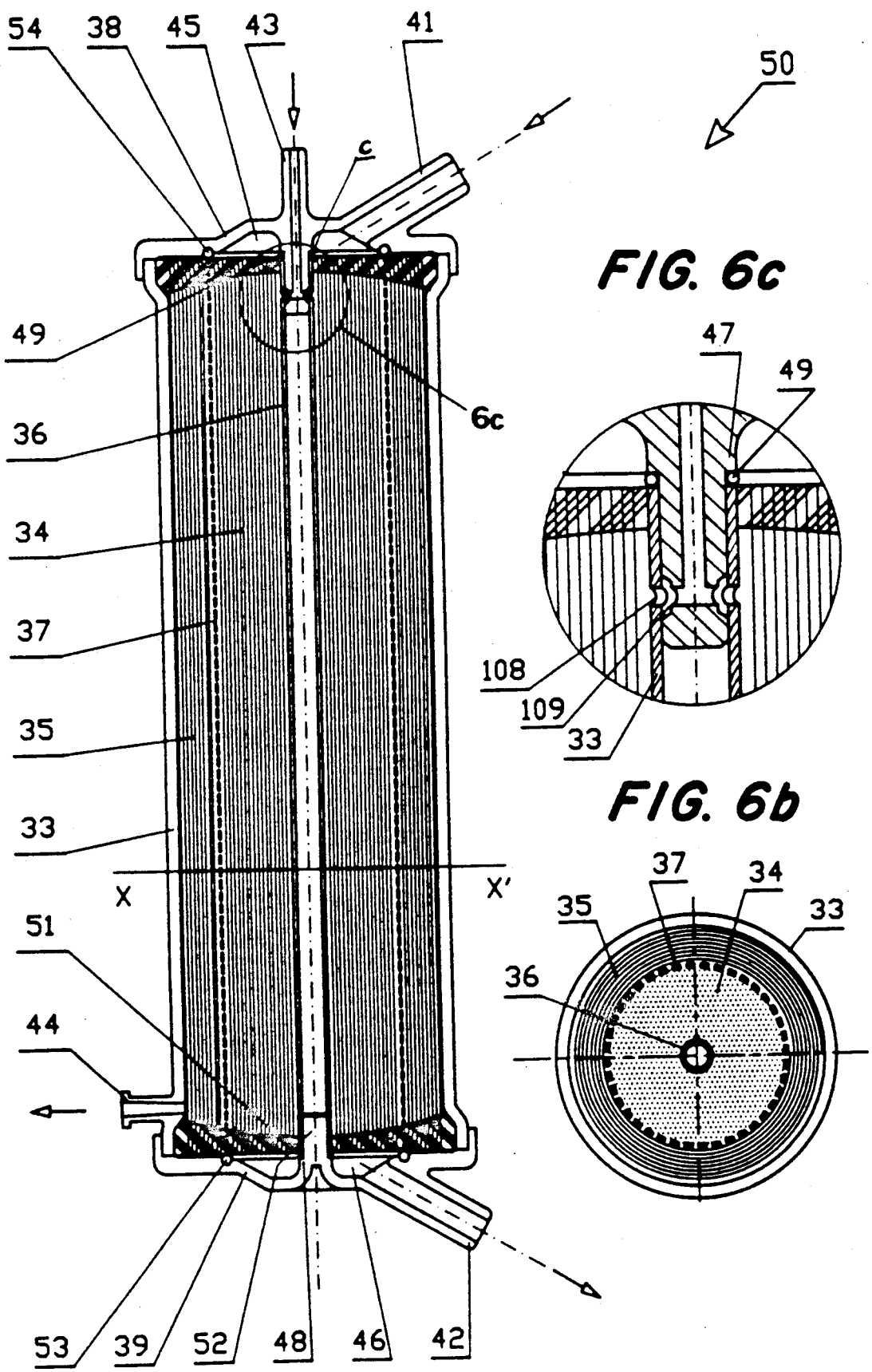

INTEGRATED DEVICE FOR THE BIOSPECIFIC PURIFICATION OF A LIQUID CONTAINING CELLULAR ELEMENTS

BACKGROUND OF THE INVENTION

1. Field of the Invention

The present invention relates to a device for treating biological liquids to remove undesirable substances contained therein, and more specifically to a device for filtering and biospecifically purifying biological liquid such as blood.

2. Description of The Related Art

At present there are many pathologies associated with the presence of undesirable components in the blood. It is, therefore, worthwhile to have the capability to selectively clear the blood of these substances. Many devices have been proposed for this purpose.

French patent application 2,035,134 proposes a device for eliminating proteins or specific amino acids from the blood by passing blood over an active substance. However, such a device carries major drawbacks such as the risk of degrading specific elements of the blood, particularly erythrocytes thus causing hemolysis.

Since the undesirable substances that one wishes to eliminate from the blood are present in the liquid fraction of the blood which is called blood plasma, it has been proposed to treat only the blood plasma. French Patent Application 2,325,390 discloses this type of a first device for separating the plasma from the specific elements of the blood and a second device in series with the first device for purifying the plasma. Although this system has the advantage of not requiring contact between the specific elements of the blood and the treatment agent contained in the purification device, it has the drawback of requiring the circulation of a considerable quantity of liquid plasma. Since this quantity is withdrawn from the patient's blood circulation, it is very important to minimize the amount withdrawn as much as possible.

In European Patent Application E-P 139,949 a device has been proposed comprising an internal bundle of hollow fibers constituting a semipermeable membrane, and intended to separate the plasma from the specific elements of the blood. This bundle of hollow fibers is surrounded by a treatment chamber containing an agent for treating the plasma. The blood, circulating inside the hollow fiber is treated through filtration by the agent. This device uses the processes of filtration and retrofiltration. As the blood to be treated enters the first section of the device, the pressure of the blood inside the fibers causes plasma to pass from the inside of the fibers towards the treatment chamber by convection. Conversely, in the second section, near the outlet of the device, the pressure of the blood inside the fibers is lower than the pressure of the plasma in the treatment chamber, causing the plasma to filter back and rejoin the blood enriched with specific elements. The plasma obtained by filtration of the blood through the wall of the hollow fibers is treated by an agent contained in the treatment chamber. Therefore, a recombination of the specific elements of the blood with the purified plasma is obtained in the second section of the device, and flows through the outlet.

Although this system remedies a certain number of drawbacks of the prior art, it has the disadvantage of being limited by the plasma filtration flow through the semi-permeable membrane. In fact, in order for the processes of filtration and retrofiltration to be used for plasmapheresis, the difference in pressure on either side of the membrane must cancel out at the center of the module, requiring a zero flow of filtration at that point.

To increase overall plasmafiltration flow, it is necessary to either increase the filtration surface, the blood flow, or the drop in pressure of the blood inside the device. In view of its limited filtration capacity, such a device does not make it possible to meet present performance requirements.

U.S. Pat. No. 4,361,484 proposes a blood purification device having a microporous membrane, wherein the pores on a portion of the membrane remote from the passing blood hold a biologically active substance. The patent also discloses a purification device comprising means for subjecting the blood to be purified to pressure variations so as to produce an alternating passing of a fraction of the blood through the micropores of the membrane. Thus, only the plasma fraction of the blood to be purified penetrates through the micropores of the membrane and comes into contact with the biologically active substances.

Such a device eliminates the preliminary stage of plasma filtration and prevents contact between the blood cells and the biologically active substances. However, apart from being complicated to operate, such a device presents serious manufacturing difficulties. Moreover, it seems difficult to attain an adequate purification rate with such a device.

Thus, the biospecific purification devices of the prior art do not allow for satisfactory treatment of a biological liquid such as blood.

An object of the present invention is to provide a biospecific purification device, not having the drawbacks of the prior art and permitting good purification of a biological liquid such as blood without the risk of destroying cells.

Another object of the present invention is to provide a biospecific purification device, not requiring the circulation of a large quantity of liquid.

Another object of the present invention is to provide a biospecific purification device that is easily manufactured at low cost.

Another object of the present invention is to provide a biospecific purification device with good efficiency relative to the size and bulk of the device.

Another object of the present invention is to provide a biospecific purification device which is simple to operate, reliable, and has all the necessary patient safeguards.

The foregoing objects are provided by a device for biospecifically purifying a liquid having a first portion containing cellular elements and a second portion without cellular elements, said device comprising, a casing means for conducting said liquid into said casing, means disposed within said casing for tangentially filtering said first portion from said second portion, means disposed within said casing for transversely filtering said second portion to biospecifically purify the liquid after the separation of said cellular elements, means for evacuating said first portion and said second portion from said casing.

Additional objects and advantages of the invention will be set forth in the description which follows, and in part will be obvious from the description or may be learned by practice of the invention. The objects and advantages of the invention may be realized and attained by means of the instrumentalities and combinations particularly pointed out in the appended claims.

BRIEF DESCRIPTION OF THE DRAWINGS

FIG. 5b illustrates the interconnection of a plurality of the devices depicted in FIG. 5a.

FIG. 6a is a longitudinal cross-sectional view of a device in accordance with a fifth embodiment of the present invention.

FIG. 6b is a transverse cross-sectional view taken along the plane XX' in FIG. 6a.

FIG. 6c is an enlarged view of the area within circle C in FIG. 6a.

FIG. 7b is a transverse cross-sectional view taken along the plane YY' in FIG. 7a.

FIG. 7c is an enlarged view on the area within circle C in FIG. 7a.

FIG. 8b is a transverse cross-sectional view taken along plane ZZ' of FIG. 8a.

FIG. 9b is a transverse cross-sectional view taken along plane PP' of FIG. 9a.

FIG. 10b is a transverse cross-sectional view taken along plane KK' of FIG. 10a.

DESCRIPTION OF THE PREFERRED EMBODIMENTS

Figure 1:
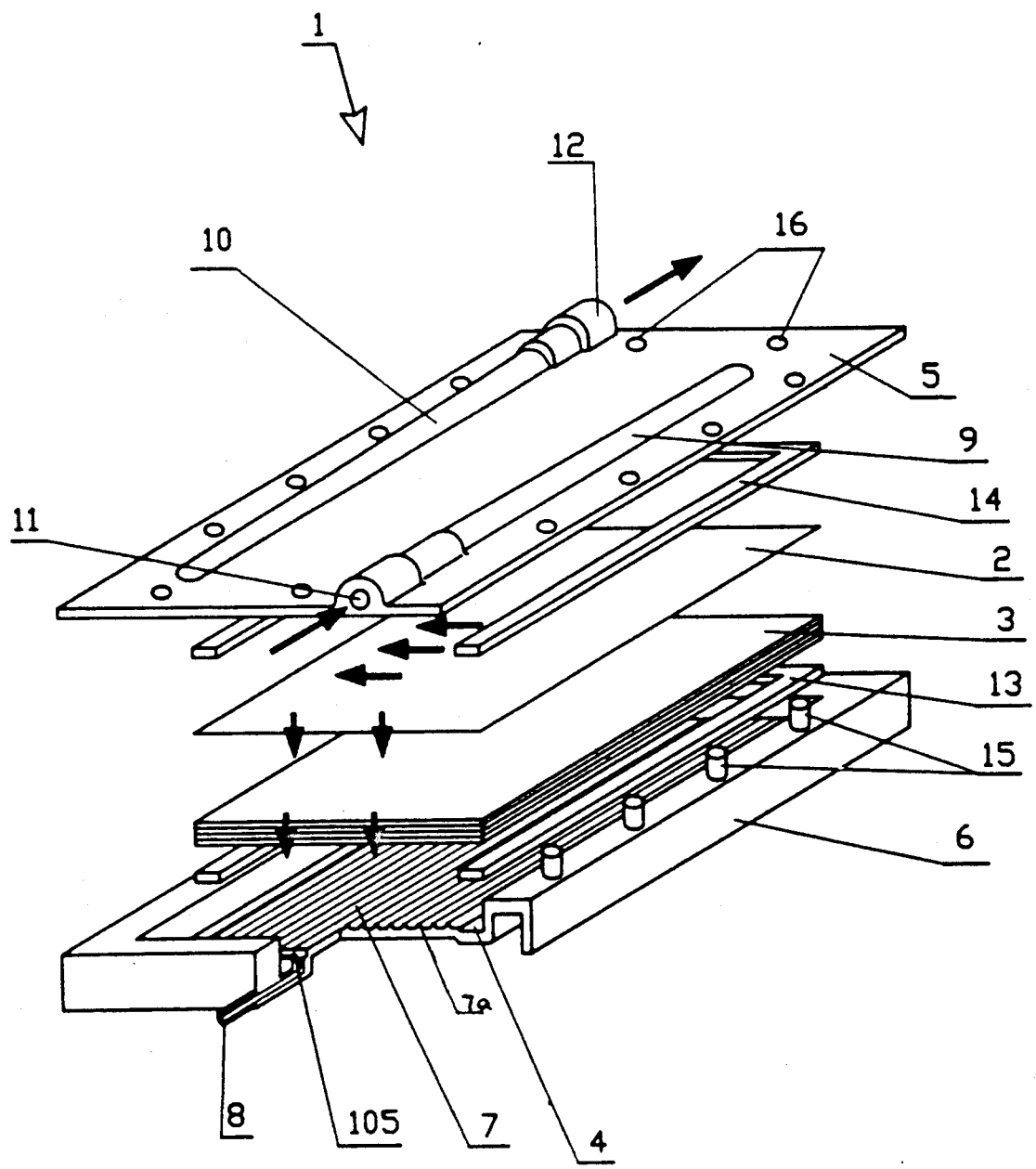
FIG. 1 is an exploded view of a first embodiment of a device in accordance with the present invention.

Reference will now be made in detail to the present preferred embodiments of the invention as illustrated in the accompanying drawings. For the sake of simplification, similar elements of the various figures will be referred to by the same reference numerals.

Referring to FIG. 1, purification device 1 comprises flat membrane 2 for filtering the liquid to be treated, and microporous structure 3 that includes a stack of flat biospecific purification membranes. This membrane assembly is disposed inside an enclosure including lower plate 4 and upper plate 5.

Lower plate 4 has, on its periphery, raised portion 6 constituting the lateral walls of purification device 1.

The internal face of lower plate 4 is provided with longitudinal grooves or any other appropriate network of grooves 7a. Grooves 7a may be continuous, discontinuous sinusoidal, or zig-zag grooves intended to promote the collection and circulation of the liquid obtained after it has been filtered through the set of membranes. This network of grooves defines a working zone 7 for the circulation of the purified liquid.

A transverse duct 105 is provided at the end of the working zone 7 for collecting the purified liquid.

Lower plate 4 is also provided with duct 8 formed in the lateral wall 6 at one of the ends of working zone 7. Duct 8 is disposed to allow for fluid communication between the exterior and interior of the device.

Upper plate 5 is provided with two lateral elongated ducts 9 and 10 extending longitudinally and substantially parallel to each other. Ducts 9 and 10 are respectively intended for the distributing liquid to be treated and for collecting the liquid containing a concentration of cellular elements. They are disposed on upper plate 5 for fluid communication between the exterior and interior of purification device 1. Duct 9 includes inlet 11 for the intake of liquid to be treated, and duct 10 includes outlet 12 for evacuating liquid with a concentration of cellular elements.

Opening 11 is disposed on plate 5 on an edge opposite opening 12. This arrangement makes it possible to ensure good circulation of the liquid to be treated by avoiding the formation of a stagnation zone referred to as a "dead zone".

The contour of the ducts 9 and 10 is such that their cross section decreased in a substantially constant way from the openings 11 and 12. This functions to promote the distribution of the liquid to be treated by maintaining a substantially constant flow throughout each of the ducts.

To ensure that the liquid to be treated is distributed evenly along the film between ducts 9 and 10, the upper plate 5 is provided with ribs or stops (not shown) disposed at regular intervals on its inner face. Due to a tight grip with a constant pressure when the device is assembled, these ribs or stops ensure a substantially constant interspacing between the upper plate 5 and filtration membrane 2 over the entire surface of the membrane.

Filtration membrane 2 is a flat membrane permitting the separation by tangential filtration of the cellular elements from the liquid to be purified.

When the liquid to be purified is blood, filtration membrane 2 is, for example, a plasmapheresis membrane ensuring the separation of the plasma from the blood cells. An example of a membrane being particularly well suited for blood is the TPC 19 membrane manufactured by RHONE-POULENC. The method of manufacturing this membrane is described in French Patent Application number 82/00485.

Microporous structure 3 for biospecific purification is, for example, constituted by a set of flat microporous membranes appropriately treated to ensure the biospecific purification of the liquid obtained by tangential filtration along membrane 2. Microporous structure 3 may include materials having reactive chemical groupings permitting the grafting of purifying molecules. By way of example and not limitation, these molecules include proteins, glycoproteins, polysaccharides or more generally organic derivatives of a natural, synthetic or semisynthetic origin having a biospecific affinity for the derivatives to be purified. For example, Biodyne Immuno-Affinity Membranes sold by the Pall Company can be used. Antibodies are grafted to the membrane by direct covalent fixation. The antibodies are chosen for their ability to recognize and selectively link up with complementary substances that must be eliminated from the liquid to be purified.

It is also possible to use the Immobilon membrane sold by the Millipore Company. Using this type of membrane specific proteins such as antibodies which are capable of selectively reacting with the substance to be purified are grafted to the membrane by covalent bonding.

To obtain an adequate treatment surface for all the liquid to be purified several flat membranes may be stacked on top of one another. Instead of using a stack of flat membranes, a single microporous membrane making it possible to obtain a treatment surface equivalent to that of the stack may be used.

The microporous structure may also be made of any other appropriate substances, such as a sheet of a non-woven material with a considerable interstice rate, a material with fibers or pellets, or even by an assembly of filaments.

The arrangement of the various elements constituting the purification device 1 is as follows. Microporous structure 3 consisting of a stack of purification membranes is disposed on lower plate 4 within the enclosure defined by raised edges 6. Frame gasket 13 provides a seal between lower plate 4 and microporous structure 3. Filtration membrane 2 is disposed on microporous structure 3 for separating the cellular elements from the liquid to be purified by tangential filtration. For example, the membrane may be used to separate blood cells from plasma, where the liquid to be purified is blood. The membrane is sealed with the upper plate 5 using frame gasket 14 which is of the same type as gasket 13.

These gaskets can be replaced by any equivalent mean such as a peripheral fixing of the membranes with a polyurethane glue.

A plurality of assembly dowels 15 are disposed along the raised edges 6 of the lower plate 4. Dowels 15 are inserted in corresponding holes 16 disposed on the periphery of the upper plate 5 for assembly of the purification device. This structure makes it possible to assemble the purification device by processes such as ultrasonic riveting or thermoforming.

The purification device 1 integrates into a single casing a filtration membrane for the liquid to be purified, as well as microporous structure for biospecific purification.

The operation of the purification device 1 is as follows. The liquid to be treated is introduced into the duct 9 through the inlet 11. Duct 9 distributes the liquid to be treated over the entire length of the upper plate 5. This liquid is then spread in the form of a film between the inlet duct 9 and the outlet duct 10. The direction of liquid flow is indicated by arrows in FIG. 1. This circulation of the liquid to be treated in the form of a film allows certain elements to be separated from the liquid by tangential filtration along the filtration membrane 2. When the liquid to be purified is blood, the tangential filtration of the blood along plasmapheresis membrane 2 allows the blood plasma transversing the membrane to be separated from the cellular elements which, because of their size, are retained and are discharged to the outside of the device through duct 10 and outlet 12. The liquid filtrated through membrane 2 is then filtered by transverse filtration through the stack of purification membranes. Thus, all the liquid to be purified traverses the microporous structure represented by the stack of purification membranes.

The purifying molecules grafted on to the surface and into the micropores of the purification membranes selectively retain the molecules intended to be eliminated during the transverse passing of the liquid to be purified. The liquid thus purified is collected in a network of grooves 7 on lower plate 4, before being discharged to the outside through outlet 8.

When the liquid to be purified is blood, the plasma obtained after tangential filtration along membrane 2 is purified by transverse filtration through the purification membranes. The purified plasma is discharged outside the device through outlet 8. This plasma may then be recombined with the cellular elements coming from outlet 12 to be subsequently returned to the patient.

The present invention, therefore, makes it possible to integrate in a single casing, means for tangential filtration immediately followed by transverse filtration.

Figure 2:
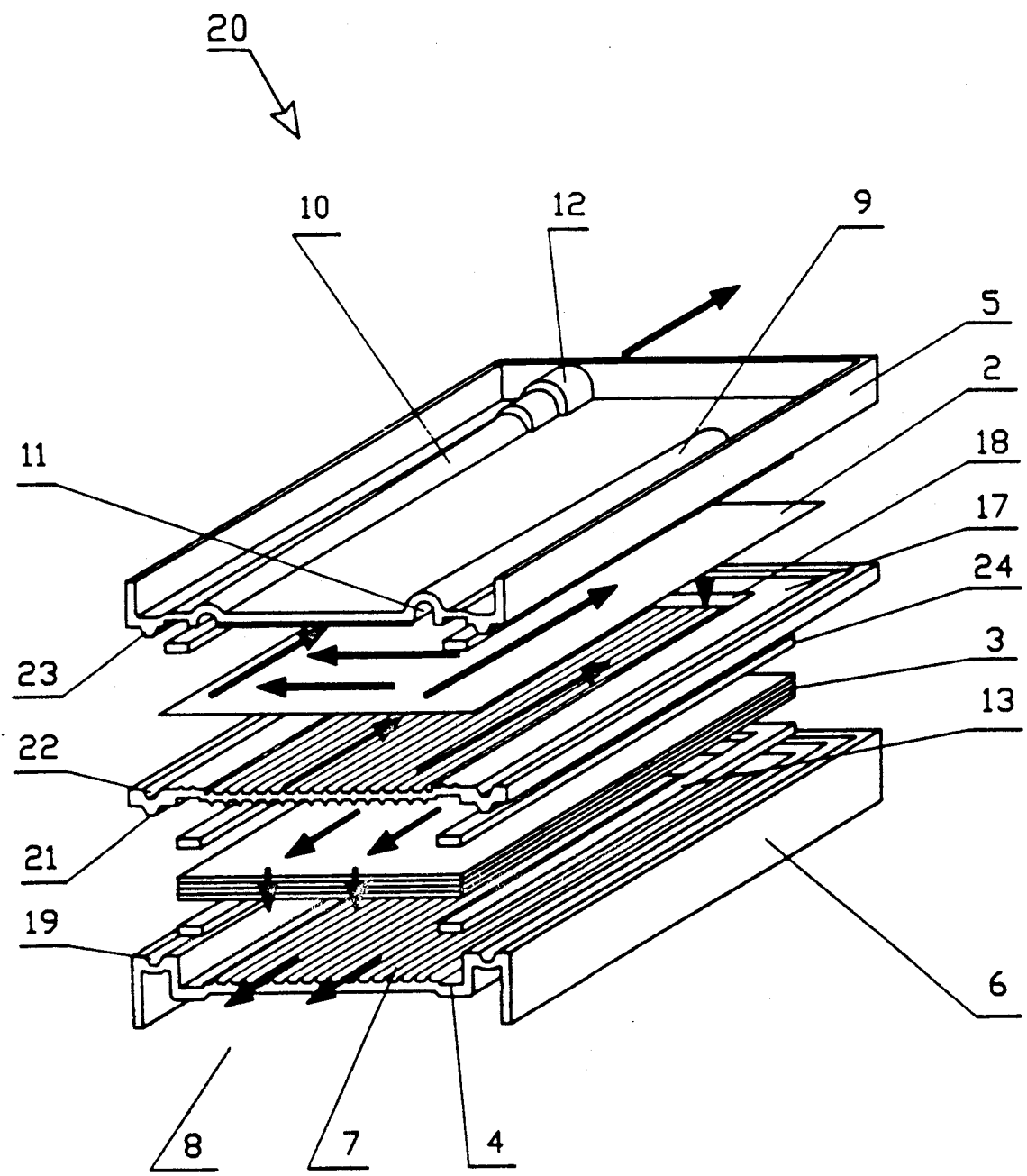
FIG. 2 is an exploded view of a second embodiment of a device in accordance with the present invention.

According to a second embodiment of the invention depicted in FIG. 2, purification device 20 includes intermediate plate 17 disposed between filtration membrane 2 and microporous structure 3. Intermediate plate 17 constitutes a support for filtration membrane 2 and thus makes it possible to ensure a substantially constant spacing between the upper plate 5 and filtration membrane 2 even where the assembly of the device is effected on the basis of constant dimensions, which from a practical point of view, is preferable to an assembly on the basis of constant pressure. This allows a substantially even distribution liquid to be treated between intake duct 9 and outlet duct 10.

Intermediate plate 17 is provided with grooves on each of its faces defining a working zone for the circulation of the filtered liquid to be purified. This working zone is similar to the network of grooves of the inner face of lower plate 4. Passageway 18 is provided at one of the ends of this working zone, preferably on the side opposite inlet 11, to allow the filtered liquid collected on one of the faces of intermediate plate 17 to spread along the other face of the plate before being purified by transverse filtration through microporous structure 3.

It is also possible to provide an intermediate plate 17 with holes spread over the whole of its surface. With this type of arrangement, the liquid to be purified directly passes through intermediate plate 17 to be subsequently treated by filtration through the purification membranes.

In order to simplify the assembly of the device, raised edge 6 of lower plate 4 is provided with peripheral groove 19 for receiving a corresponding projection 21. Projection 21 is located on the periphery of lower face of intermediate plate 17. Similarly, intermediate plate 17 has peripheral groove 22 on its upper face for receiving a corresponding projection 23. Projection 23 is located on the periphery of the lower face of bottom plate 5.

The respective projections and grooves can be joined by glueing or welding such as thermal welding or ultrasonic welding. The device can also be assembled by any other appropriate means such as the use of side plates (not shown) provided with dovetails which would hold the device together.

Flat seals 13 and 24 situated on either side of the stack of membrane 3 serve to seal device 20 and to maintain a sufficient gap for the circulation of liquid.

The operation of the purification device 20 represented in FIG. 2 is as follows. As indicated by the arrows in FIG. 2, the liquid to be treated is introduced through duct 9, and flows laterally toward outlet duct 10. As in the device represented in FIG. 1, this circulation of the liquid separates the cellular elements from the liquid to be purified by tangential filtration along the filtration membrane 2. The filtered liquid is then collected in grooves located on the upper surface of intermediate plate 17. The filtered liquid flows towards passageway 18 disposed at the end of plate 17. The liquid then flows through passageway 18 and along the grooves disposed on the lower surface of intermediate plate 17.

The liquid is then transversely filtered through the stack of microporous membranes 3 resulting in biospecific purification. Finally, the liquid is collected and transported along the spaces between the ribs of the lower plate 4 to duct 105 and discharged through outlet 8.

Figure 3:
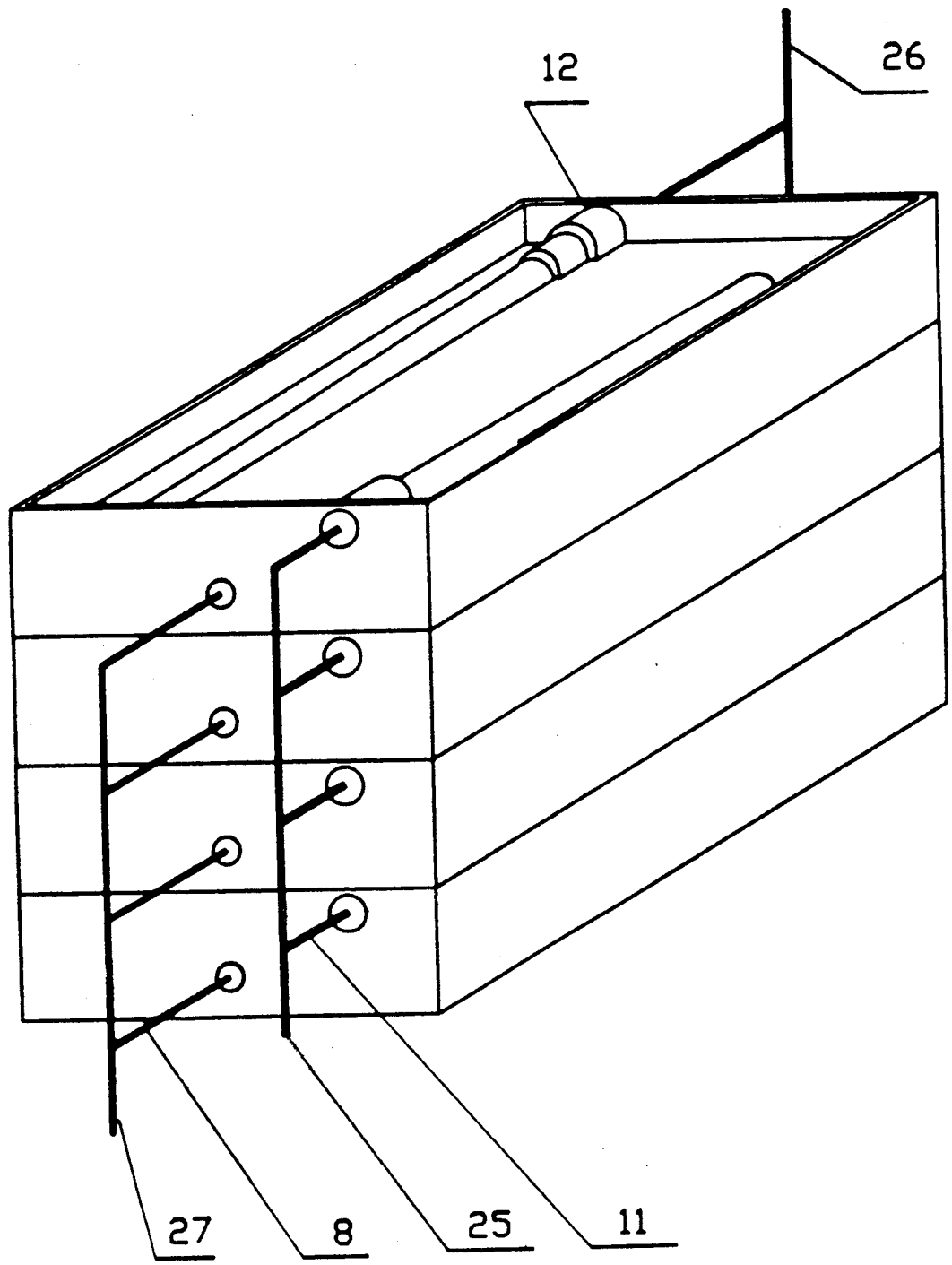
FIG. 3 depicts the interconnection of a plurality of the devices depicted in FIGS. 1 or 2.

In situations where filtration membrane 2 and the microporous structure 3 inadequately treat the liquid, it is possible to place several purification devices in parallel as represented in FIG. 3. When attached in parallel, inlets 11 are joined by line 25. Similarly, outlets 12 for the liquid containing the concentration of cellular elements and outlets 8 for the purified liquid are respectively joined by line 26 and line 27. This parallel combination of several devices, makes it possible to multiply the treatment capacity for a liquid.

Figure 4A:
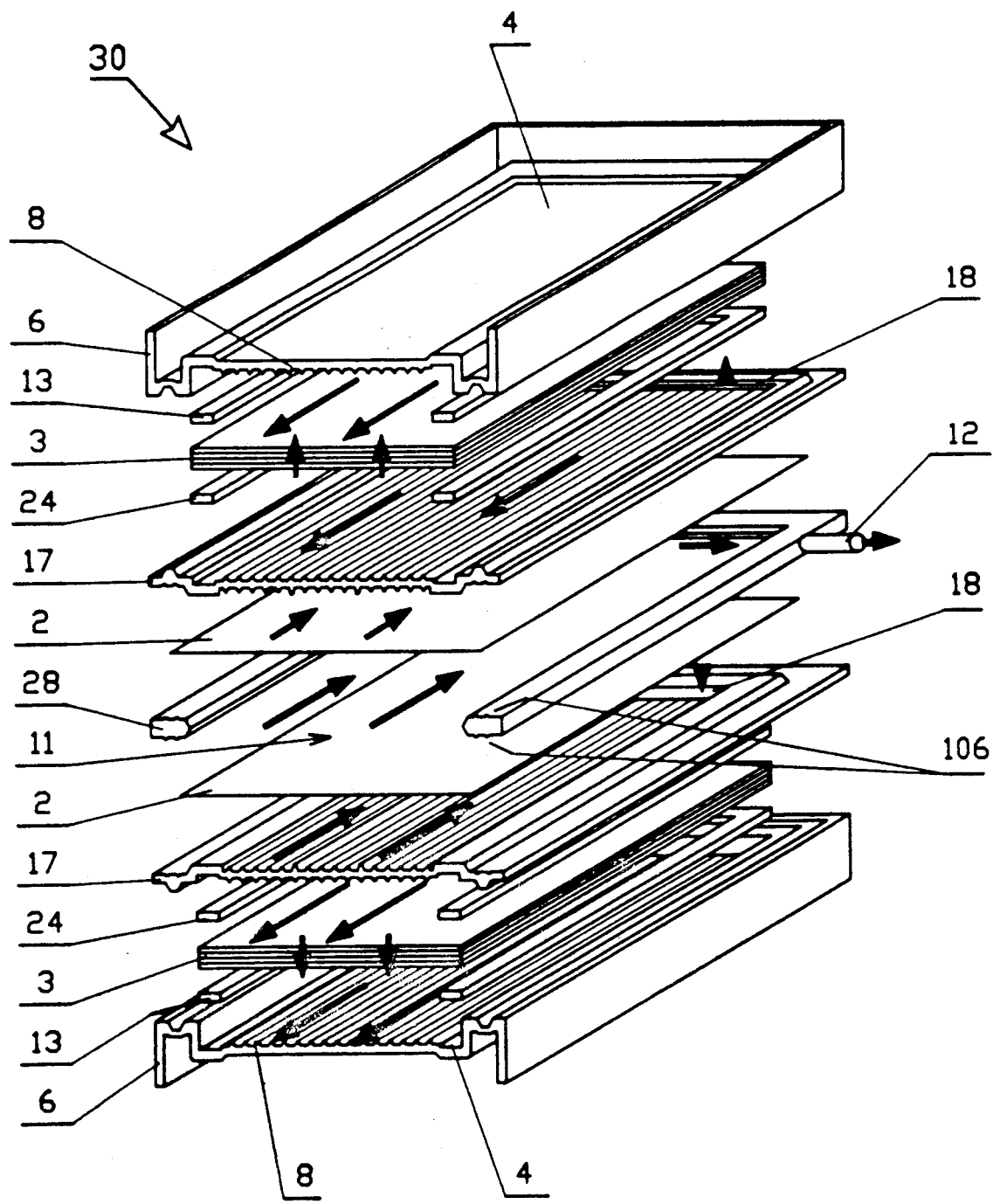
FIG. 4a and 4b each depict a device in accordance with a third embodiment of the present invention.

In the embodiment depicted in FIG. 4a, purification device 30 belongs to the flat bi-membrane type membrane. Device 30 comprises, a single inlet 11 for the liquid to be treated, a single outlet 12 for the liquid with a concentration of cellular elements, and two outlets 8 for the purified liquid. Device 30 includes two purification units for the liquid to be treated, each unit comprising a filtration membrane 2, an intermediate plate 17, and a microporous structure 3. The two purification units are disposed symmetrically in relation to a median frame 28 that separates the two filtration membranes 2. Median frame 28 is provided with beadings 106 intended to form a seal with the peripheral edges of intermediate frames 17.

The liquid to be treated is introduced into the purification device through inlet 11 disposed on median frame 28 at one of the ends of the device. The liquid then flows between the two membranes 2 where it is filtered. The liquid portion containing a concentration of cellular elements is collected at the opposite end of the device and is discharged through an outlet 12 disposed on median frame 28.

The portion of liquid filtered through membranes 2 is collected along one of the faces of intermediate plates 17. This filtered liquid then flows through passageways 18 and spreads along the other face of each of intermediate plates 17. The liquid is then purified by transverse filtration passing through microporous structure 3. The filtration and purification of the liquid to be treated occurs symmetrically in each of the purification units.

Purification device 30, while retaining very compact form, substantially increases the filtration and purification capacities over the device 20 depicted in FIG. 2.

Figure 4B:
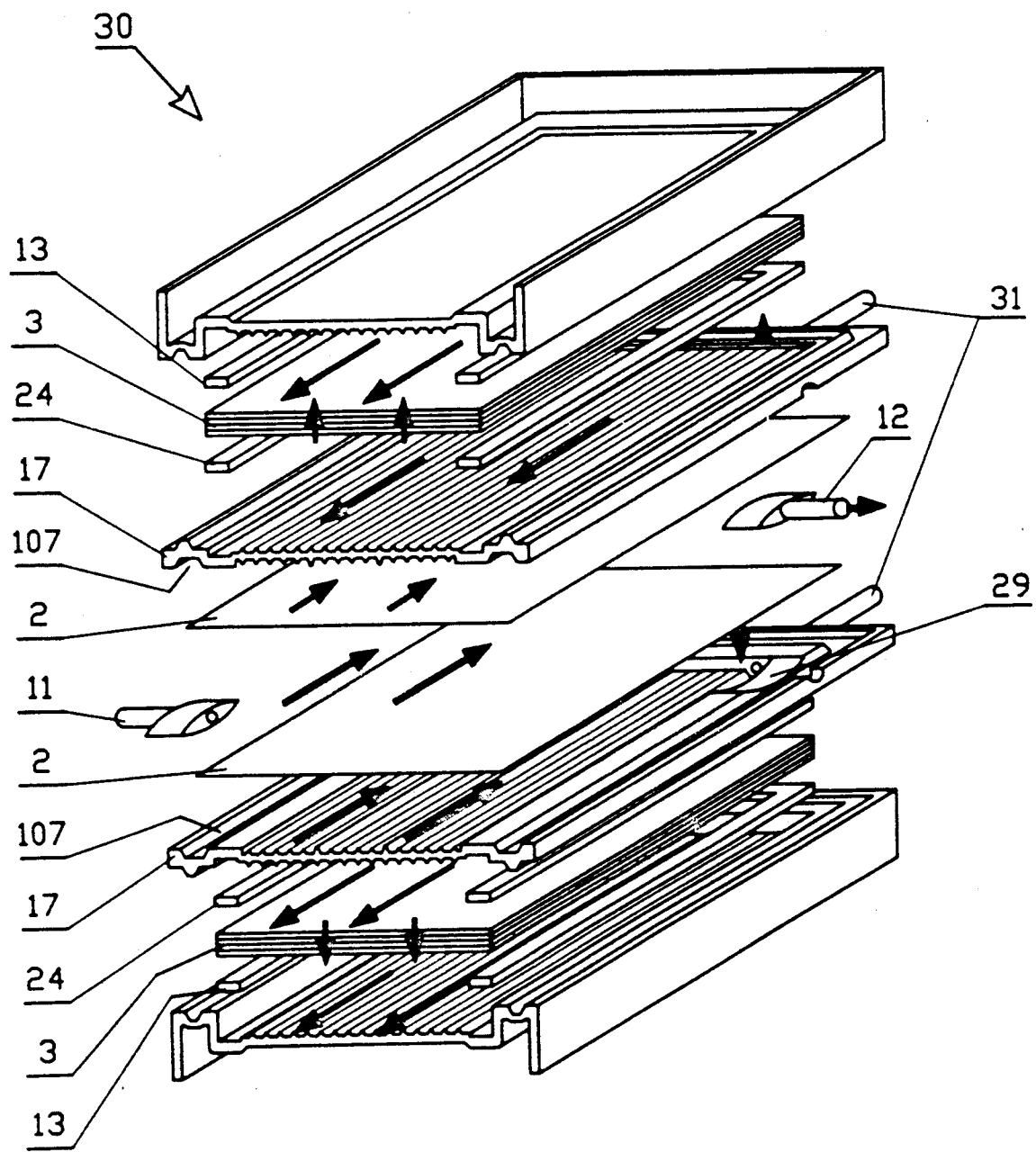

The embodiment of the invention depicted in FIG. 4b, is constructed without a median frame such as the one used in purification device 30. Intake 11 and outlet 12 comprise two end fittings disposed between cutouts 29 provided in intermediate plates 17 of the two purification units. A filling in the grooves 107 of intermediate plates 17 ensures a seal between plates 17 at the level of membrane 2. Device 30 also may comprise tubes 31 on each of the intermediate plates 17 for gauging the pressure of the plasma to be purified.

Figure 5A:
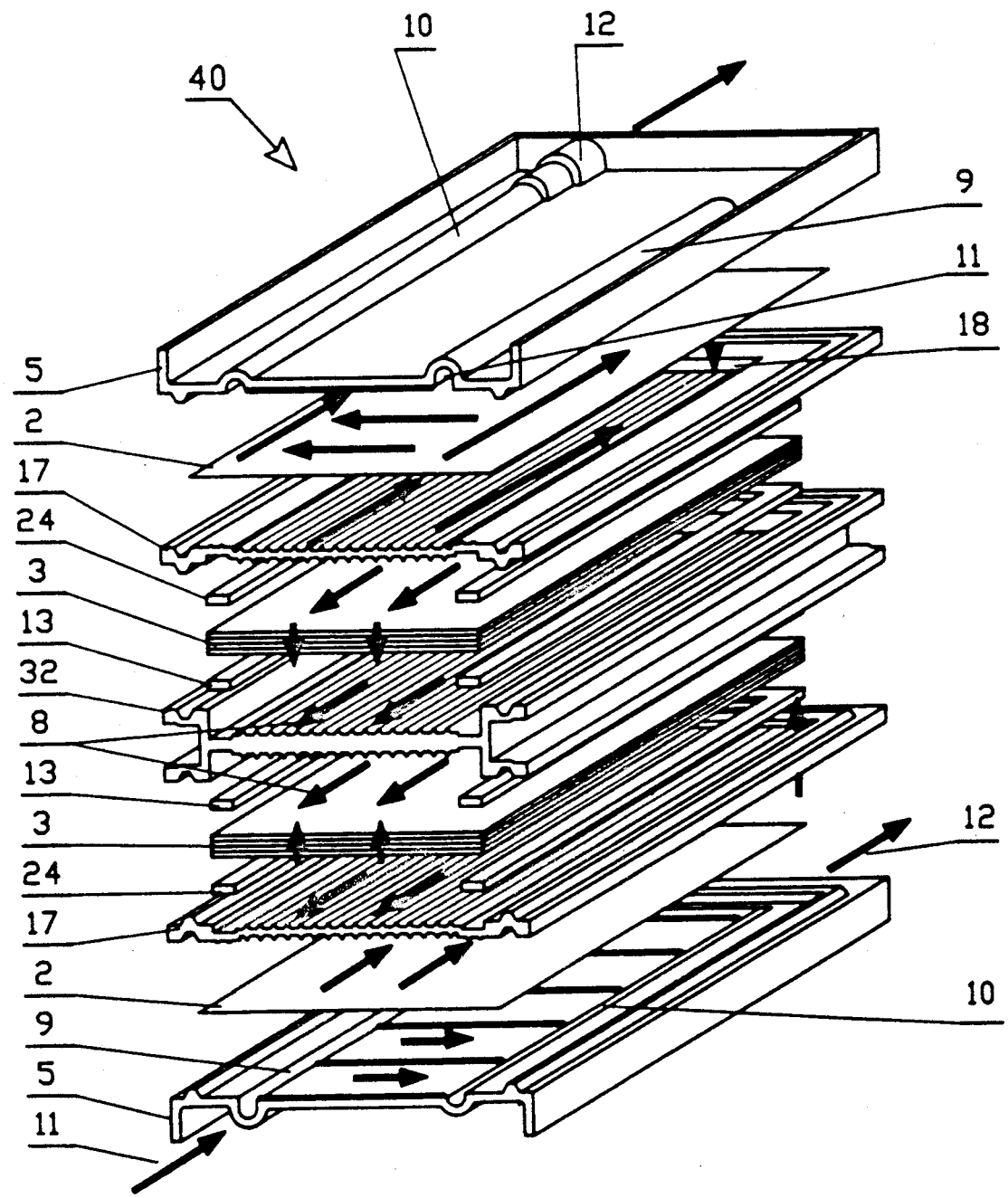
FIG. 5a is an exploded view of a device in accordance with a fourth embodiment of the present invention.
Figure 5B:
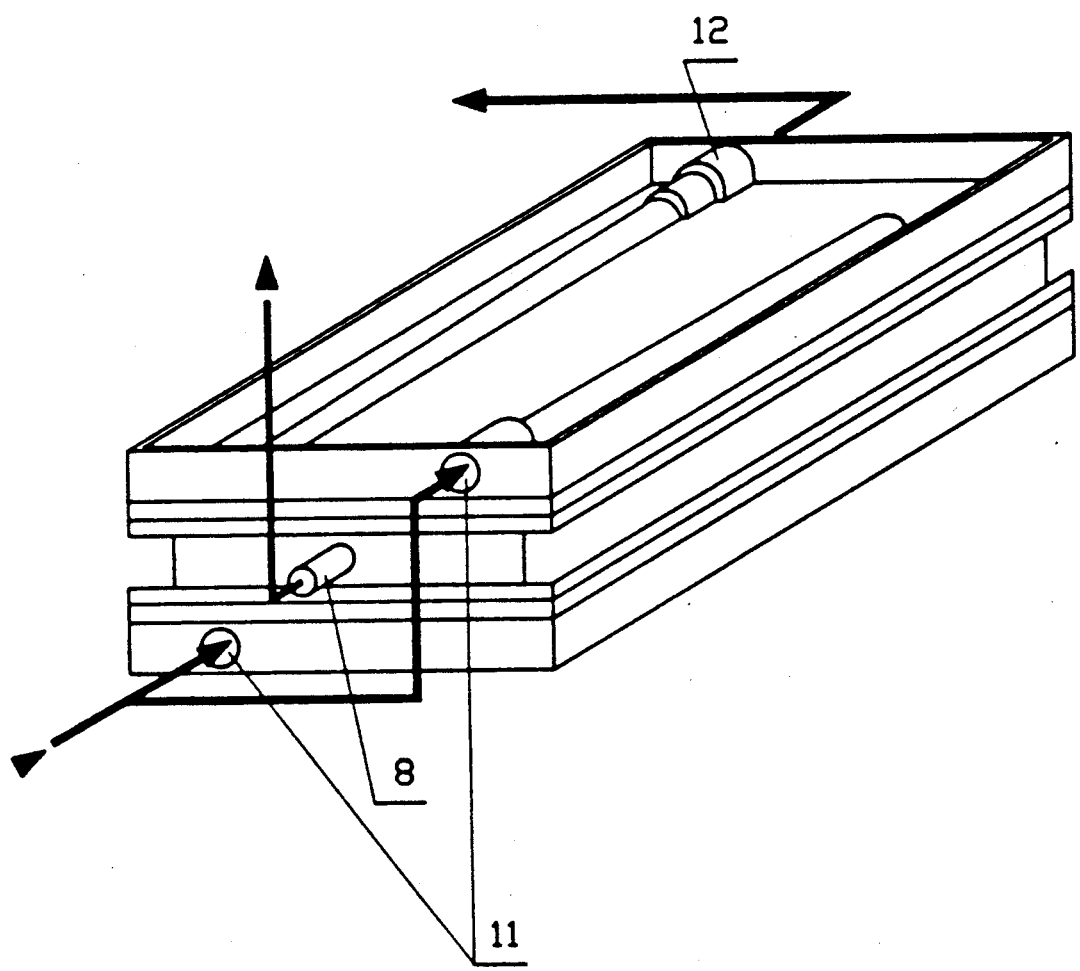

The embodiments of the invention represented in FIGS. 5a and 5b, disclose purification device 40, of the bimembrane also having flat membranes. Device 40 is similar to device 30 in that it contains two purification units. However, device 40 includes two intakes 11 for the liquid to be treated, two outlets 12 for the liquid with a concentration of cellular elements, and a single outlet 8 for the purified liquid. Device 40 comprises two outer plates 5 similar to upper plate 5 of the device 1. Device 40 also includes two lateral ducts 9 and 10 for the intake and outlet of the liquid, respectively. Each individual purification unit also comprises a membrane 2 for the separation of the cellular elements by tangential filtration, an intermediate plate 17, and a microporous structure 3 constituted by a stack of microporous membranes treated for the biospecific purification liquid.

The structure of device 40 is such that the various elements constituting each individual purification unit are assembled symmetrically in relation to central plate 32. Central plate 32 is disposed between two stacks of membranes 3 and comprises longitudinal grooves forming a working zone for the circulation of the purified liquid on each of its faces.

Liquid flow within device 40 is indicated by arrows in FIG. 5a. The liquid to be treated is introduced through each one of the ducts 9 of the plates 5. The separation of the cellular elements from the liquid to be treated is effected by tangential filtration along the filtration membranes 2.

The liquid having a concentration of cellular elements is collected in the duct 10 for discharge outside the device. The liquid obtained by filtration along membrane 2 flows over the working zone of one of the faces of the intermediate plate towards passageway 18, and is then spread over the opposite face of plate 17. This liquid to be purified then passes through microporous structure 3 constituted by the stack of purification membranes. The purified liquid is then collected in grooves disposed on each of the faces of central plate 32. The purified liquid thus obtained, is passed outside device 40 through outlet 8. Where the liquid to be purified is blood, plasma is obtained by tangential filtration along the plasma filtration membrane 2. This plasma is purified by transverse filtration through the purification membranes. The purified plasma collected in the grooves of central plate 32, is passed outside through outlet 8. The purified plasma can then be recombined with the blood containing a concentration of cellular elements coming from outlet duct 10 before being returned, for example, to a patient from whom the blood to be purified originates.

According to the preferred embodiment of the invention depicted in FIGS. 6a, 6b, and 6c, purification device 50 is a device of a mixed type, comprising a flat type membrane as well as hollow fibers. Purification device 50 includes cylindrical shell 33, housing filtration membrane 34 constituted by an internal bundle of hollow fibers. Cylindrical shell 33 also houses flat microporous membrane 35 treated for the biospecific purification of liquid. The bundle of hollow fibers 34 surrounds central wrapping tube 36, and purification membrane 35 is wrapped around bundle 34. Central wrapping tube 36 can be made from materials such as polycarbonate, polyvinyl chloride or acrylonitrile-butadiene-styrene. The hollow fibers 34, as well as flat wrapped membrane 35 are sealed at each of the ends of the bundle, in a common potting resin, such as of polyurethane.

In order to facilitate the potting operation and hold the bundle of hollow fibers 34 in place, an intercalated screen 37 can be provided between the bundle of hollow fibers and purification membrane 35. This screen is formed, for example, by a polyester fabric wherein each strand of polyester has a thickness of approximately 100 to 110 microns. The fabric marketed by the UGB Company under the designation mono TI 75-55775 is entirely suitable.

In order to facilitate the collection of the purified liquid, it is also possible to place a screen (not shown) around the bundle of hollow fibers and the membrane. Thus, as shown in FIG. 6b, the wrapping of the membrane 35 is effected in a continuous and uninterrupted manner. To prevent a possible spiral flow of the liquid along membrane 35 and to promote a transverse flow of liquid through the micropores, it is preferred to glue the membrane to the preceding layer at certain intervals of the wrapping along a generatrix. The potting operation, as well as the wrapping of the purification membrane can also be facilitated by attaching a fine contiguous screen to the latter.

Purification device 50 includes covers 38 and 39 at each of the ends of cylindrical shell 33. Cover 38 is provided with intake tube 41 for the intake of liquid to be treated. The internal profile of cover 38 is such that it defines annular chamber 45 for distributing the liquid to be treated. As shown in FIG. 6c, an axial portion of the cover extends slightly inside the bundle of hollow fibers. The axial portion is supported by shoulder 47 that also supports axial tube 43 that extends outside cap 38. Tube 43 is connected to means (not shown) for measuring the pressure of the filtered liquid to be purified. This gauging of the pressure is made possible by openings 108 in central tube 36 that communicates with tube 43 by way of peripheral groove 109. The distribution chamber 45 is sealed by two O-rings 49 and 54.

Cover 39 is provided with outlet tube 42 for evacuating the liquid having a concentration of cellular elements. The internal profile of cover 39 defines annular chamber 46 for collecting the liquid. The axial portion 52 of cover 39 is supported by shoulder 48 and is inserted slightly inside the bundle of hollow fibers. The collecting chamber is sealed by two O-rings 51 and 53.

The cylindrical shell 33 also comprises tube 44 allowing the purified liquid to be discharged. Tube 44 is preferably disposed on a portion of cylindrical shell 33 proximate cover 39.

The embodiment depicted in FIG. 6a functions as follows. Liquid to be treated containing cellular elements is introduced into distribution zone 45 of cover 38 through tube 41. The liquid then penetrates hollow fibers 34 that are open towards distribution zone 45 and circulates inside the hollow fibers separating the cellular elements from the liquid to be treated by tangential filtration. When the liquid to be treated is blood, blood cells are separated from the plasma during this stage. The plasma is subsequently purified by transverse filtration through the flat microporous membrane 35, treated to ensure the biospecific purification of the liquid portion without cellular elements.

The liquid having a concentration of cellular elements is collected in a collection zone 46 of the cover 39 and is discharged to the outside through the tube 42. The purified liquid, (purified plasma) is discharged outside the device through the tube 44. This purified plasma can, if necessary, be recombined outside purification device 50 with the blood coming from tube 42 so as to reconstitute complete purified blood.

Figure 7A:
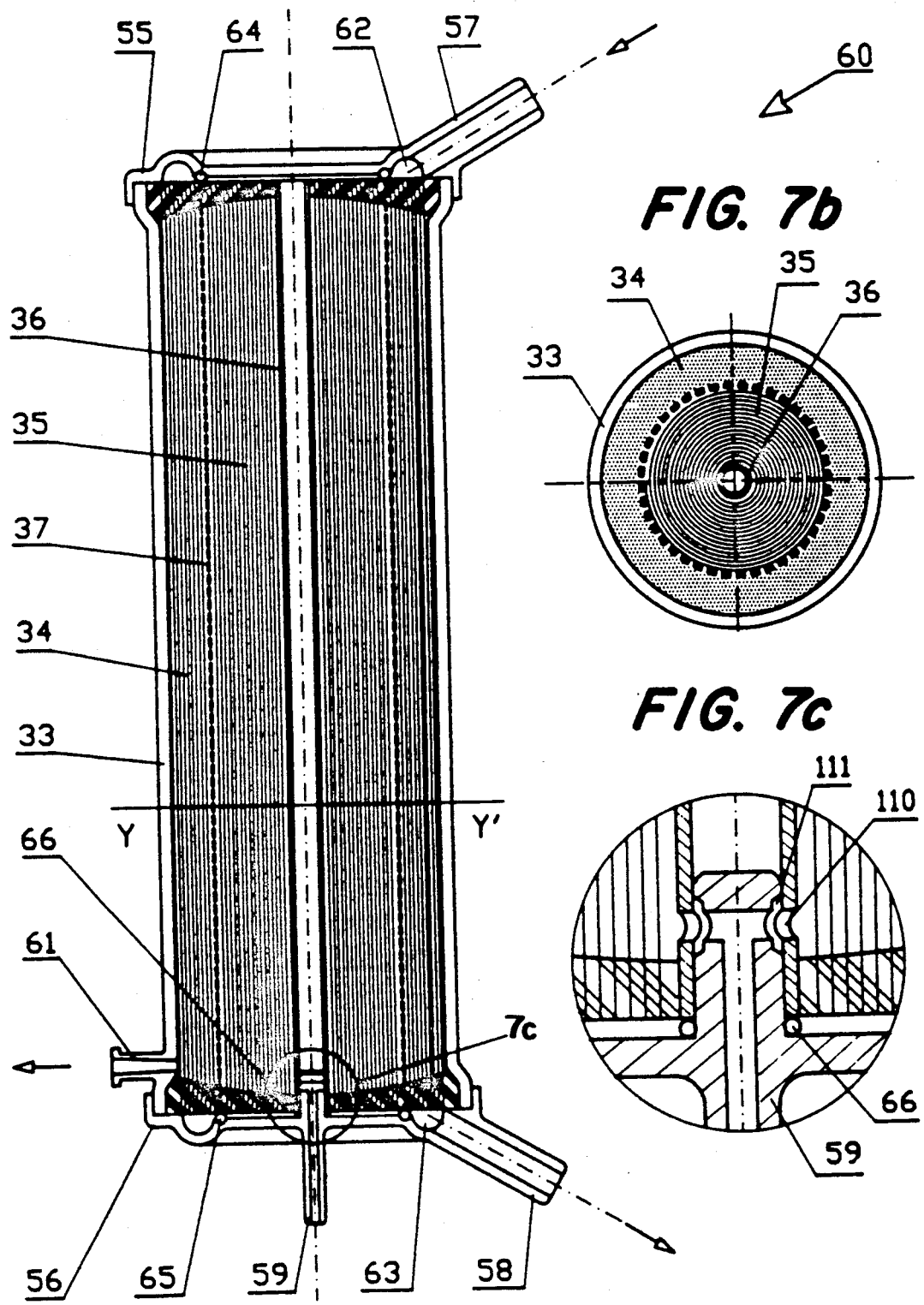
FIG. 7a is a longitudinal cross-sectional view of a device in accordance with a sixth embodiment of the present invention.
Figure 7B:
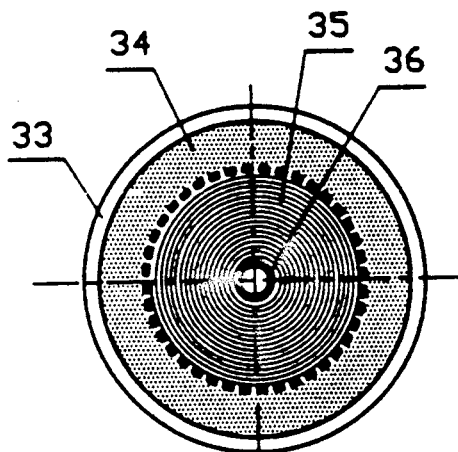
Figure 7C:
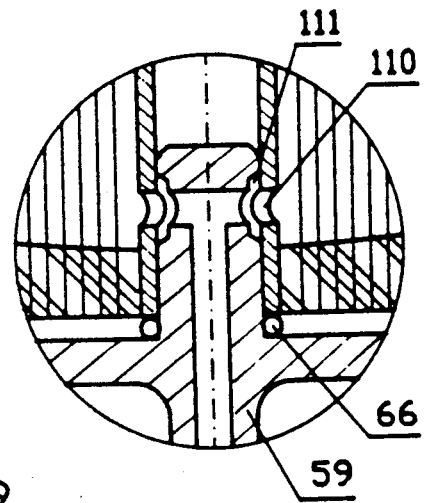

According to the embodiment depicted in FIGS. 7a, 7b and 7c, hollow fibers 34 for the tangential filtration of the liquid to be treated are disposed at the periphery of purification device 60, while the biospecific purification membrane 35 is wrapped around tube 36. In this embodiment, it is desirable to include an internal screen (not shown) around wrapping tube 36, and to include flow channels on tube 36 in order to facilitate the circulation of purified liquid.

Cover 55 is provided with intake tube 57 for the liquid to be treated. Distribution zone 62 is situated at the periphery of cover 55. O-ring 64 is disposed proximate distribution zone 62 for sealing distribution zone 62. The position of O-ring 64 corresponds to the location of intercalated screen 37.

Cover 56 is provided with outlet tube 58 for the liquid having a concentration of cellular elements. At its axial portion, cover 56 also includes tube 59 for the outlet of the purified liquid, as shown in FIG. 7c. The purified liquid is collected in tube 59 via peripheral groove 111 disposed on the portion of the cover inserted within wrapping tube 36 proximate tube openings 110.

The seal between the membrane 35 and the tube 59 is provided by O-ring 66. Collecting zone 63 for the liquid having a concentration of cellular elements is situated at the periphery of cover 56. The seal is ensured by O-ring 65. Cylindrical shell 33 also includes a tube 61 for gauging the pressure of the filtered liquid to be purified.

Figure 8A:
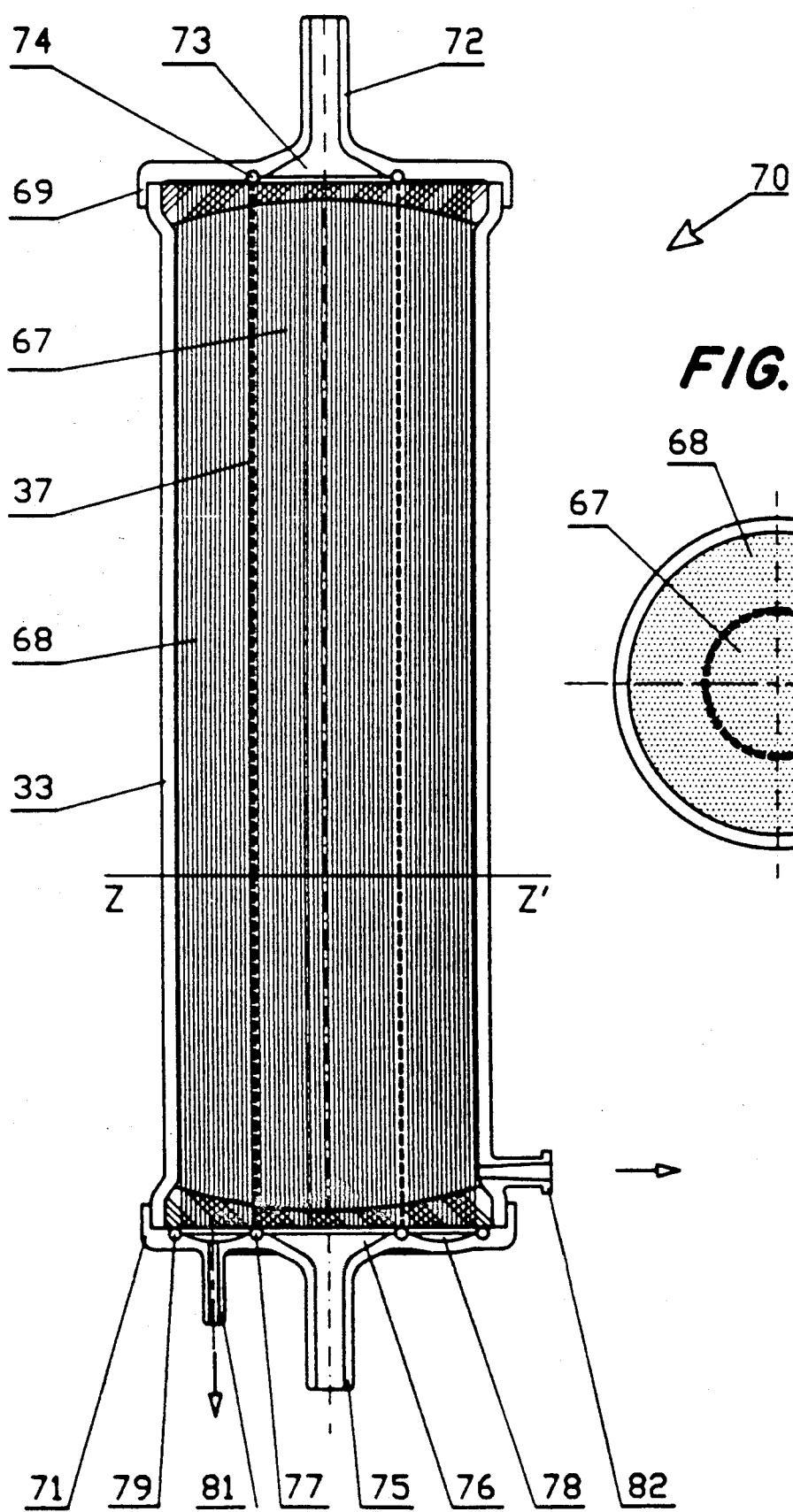
FIG. 8a is a longitudinal cross-sectional view of a device in accordance with a seventh embodiment of the present invention.
Figure 8B:
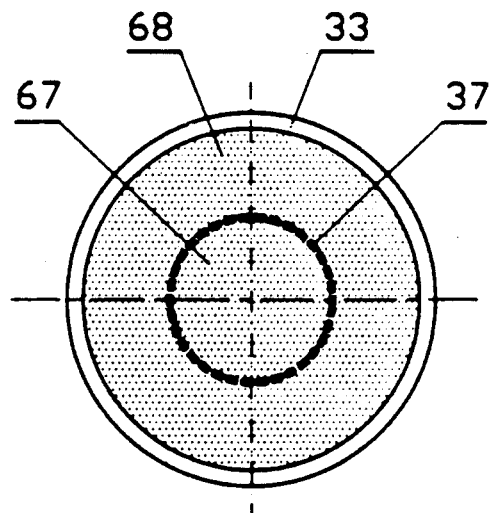

According to the embodiment depicted in FIGS. 8a and 8b, purification device 70 includes inner bundle of fibers 67 for the tangential filtration of the liquid to be purified and outer bundle of fibers 68 treated for biospecific purification. The two bundles are separated by an intercalated screen 37 and are disposed inside cylindrical shell 33. Hollow fibers 67 and 68 are potted at each of the ends of the device by means such as polyurethane glue. Device 70, like devices 50 and 60 includes two covers 69 and 71. Cover 69 is provided with axial tube 72 intended for the intake of the liquid to be treated. The profile of the cover 69 is such that a distribution zone 73 for the liquid to be treated communicates with the inside of the hollow fibers 67 situated at the center of device 70. O-ring 74 ensures the seal of the distribution zone 73 in an area corresponding to the position of intercalated screen 37. Cover 71 is provided with an axial tube 75 for discharging liquid with a concentration of cellular elements. Tube 81 is provided at the periphery of cover 71 intended for discharging the purified liquid. The internal profile of the cover 71 is such that it forms a central collecting zone 76 for the liquid having a concentration of cellular elements. The interiors of hollow fibers 67 opens into collecting zone 76. In addition, an annular collecting zone 78 for the purified liquid is formed by a peripheral groove, disposed on the inner face of cover 71. The seal of this collecting zone is ensured by two O-rings 77 and 79.

Peripheral shell 33 also includes tube 82 for gauging the pressure of the filtered liquid to be purified.

The operation of purification device 70 will now be described. The liquid to be treated is introduced into distribution zone 73 through the tube 72. The liquid then penetrates inside the hollow fibers of inner bundle 67. Circulation of liquid inside these fibers 67 separates the cellular elements from the liquid by tangential filtration along the walls of the fibers. The liquid with a concentration of cellular elements is collected in zone 76 is then discharged through tube 75. The filtered fraction of the liquid to be treated passes through the intercalated screen 37 and penetrates walls of hollow fibers 68 constituting the microporous membrane. Since this membrane is treated to ensure the biospecific purification of a liquid, the liquid collected in the annular zone 78 is biospecifically pure and is discharged through tube 81.

Figure 9A:
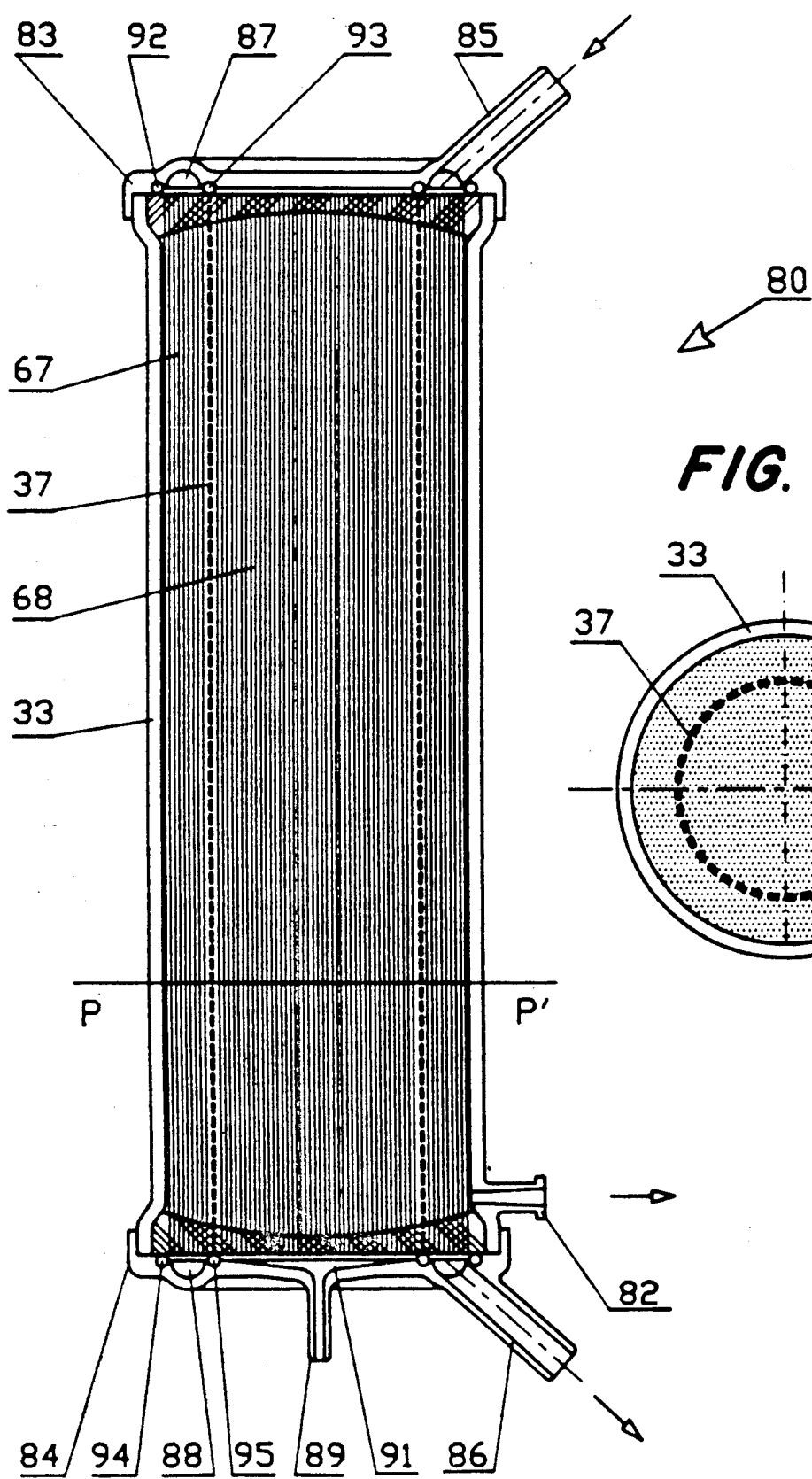
FIG. 9a is a longitudinal cross section of a device in accordance with an eighth embodiment of the present invention.
Figure 9B:
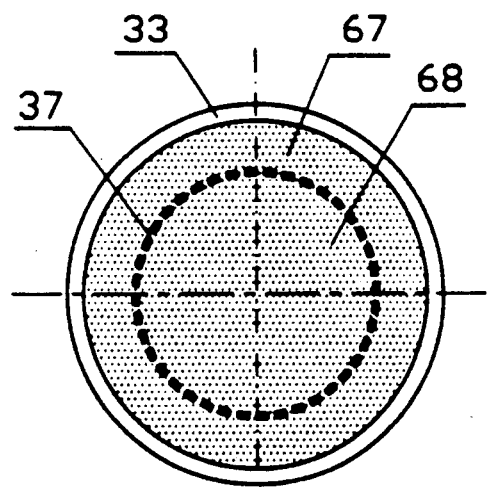

Purification device 80 represented in FIGS. 9a and 9b also includes hollow fibers. In this embodiment, hollow fibers 67 are intended for the separation of the cellular elements from the liquid to be purified by tangential filtration. Hollow fibers 67 are disposed at the periphery of the device, while hollow fibers 68, whose walls constitute the microporous structure for the biospecific purification, form the inner portion of the bundle. The two bundles are separated by an intercalated grill 37. Cover 83 is provided with a peripheral groove on its inner face defining an annular distribution zone 87 for the liquid to be treated. The seal of distribution zone 87 is ensured by two O-rings 92 and 93. Cover 84 is provided with a peripheral groove on its inner face defining collecting zone 88 for the liquid containing a concentration of cellular elements. Tube 86 extends out from zone 88 for discharging the concentrated liquid. The seal of distribution zone 88 is ensured by two O-rings 94 and 95. Additionally, the central portion of cover 84 forms collecting zone 91 for the purified liquid. Axial tube 89 extends from zone 91 for discharging the purified liquid.

Figure 10A:
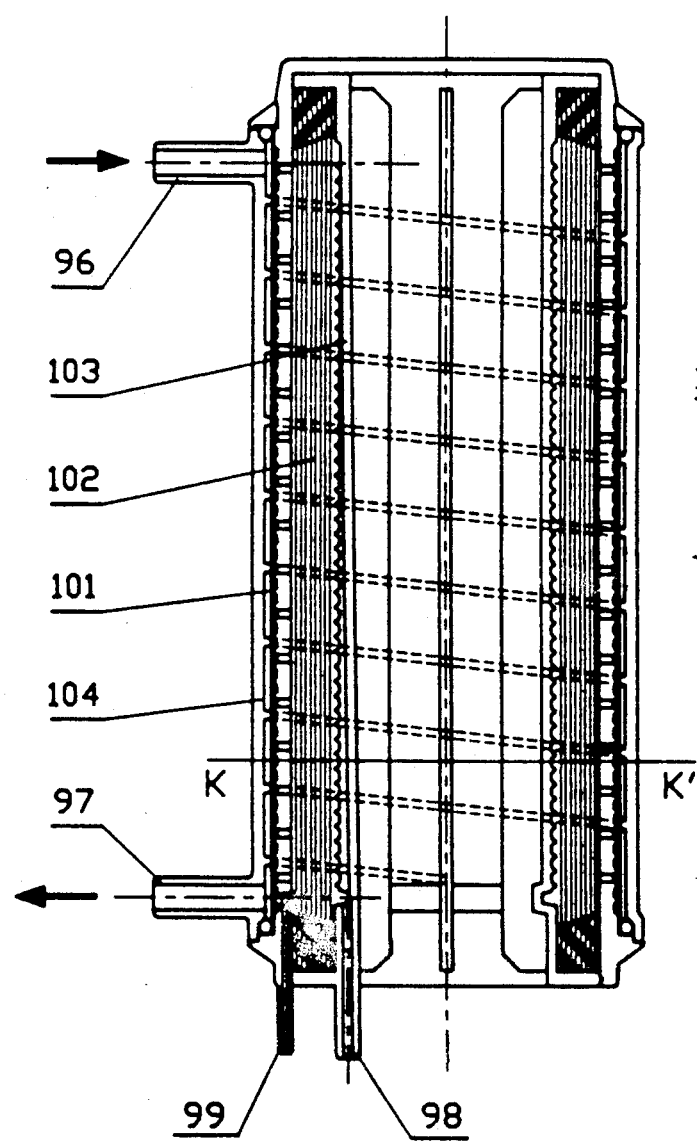
FIG. 10a is a longitudinal cross-sectional view of a device in accordance with a ninth embodiment of the present invention.
Figure 10B:
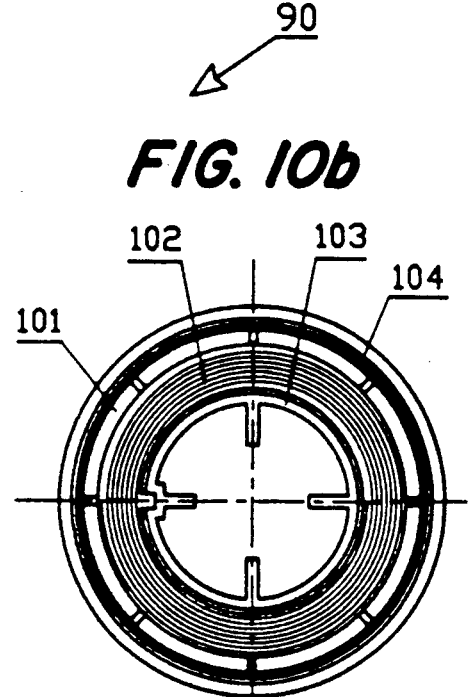

FIGS. 10a and 10b depict another embodiment of the present invention. As shown in FIG. 10a, purification device 90 includes membrane 101 for the tangential filtration of the liquid to be purified. Membrane 101 is helically disposed around biospecific microporous membrane 102. Microporous membrane 102 is a flat membrane wrapped around cylinder 103. Membranes 101 and 102 are contained in cylindrical shell 104 having tube 96 disposed on its side for the intake of the liquid to be treated. Tube 97 is also disposed on the side of shell 104 for discharging liquid having a concentration of cellular elements.

Purification device 90 also includes tube 98 for discharging purified liquid, as well as tube 99 for gauging of the pressure of the filtered liquid to be purified.

Irrespective of the embodiment chosen, the purification device which is the object of the present invention, allows a liquid to be treated successively in a single casing by tangential filtration and immediately thereafter by transverse filtration. The treated liquid is not confined to blood, but may include any other liquid containing cellular elements that one wishes to eliminate before ensuring the biospecific purification of the liquid. Thus, in the field of the biotechnologies, it is possible to ensure the treatment of a cellular suspension, such as a suspension of transformed cells or of bacteria, by first removing the cells by tangential filtration along a filtration membrane, and then by purifying the liquid by transverse filtration along the microporous structure treated to ensure the biospecific purification of the liquid. This invention is thus beneficial in isolating elements such as monoclonal antibodies or proteins produced by bacteria.

Additional advantages and modifications will readily occur to those skilled in the art. The invention in its broader aspects is, therefore, not limited to the specific details, representative apparatus and illustrative example shown and described. Accordingly, departures may be made from such details without departing from the spirit or scope of the general inventive concept as defined by the appended claims and their equivalents.

What is claimed is:

1. A device for biospecifically purifying a liquid having a first portion containing cellular elements and a second portion without cellular elements, the device comprising:
    a casing;
    means for conducting said liquid into said casing;
    means disposed within said casing for tangentially filtering said liquid to separate said first portion from said second portion;
    at least one microporous membrane sheet for transversely filtering the second portion, said microporous membrane sheet including purifying molecules grafted thereto to biospecifically purify the liquid after the separation of said cellular elements; and
    means for evacuating said first portion and second portion from said casing.

2. The device of claim 1, wherein said conducting means comprises at least one duct.

3. The device of claim 1, wherein said tangential filtration means comprises at least one membrane.

4. The device of claim 1, wherein said evacuation means includes at least one outlet duct for each filtered portion.

5. The device according to claim 1, wherein said casing includes an upper plate and a lower plate for enclosing both said tangential filtration means and said at least one microporous membrane sheet.

6. The device according to claim 5, wherein the casing further comprises an intermediate plate having a first main face and a second main face opposite the first main face, said intermediate plate being disposed between said tangential filtration means and said at least one microporous membrane sheet.

7. The device according to claim 6, wherein each main face of said intermediate plate includes a network of grooves for circulating said tangentially filtered liquid.

8. An apparatus for biospecifically purifying a liquid having a first portion containing cellular elements and a second portion without cellular elements, the apparatus comprising:
    a tubular casing;
    inlet means for flowing the liquid in an axial direction in the tubular casing;
    tangential filtration means for separating said first portion of the axially flowing liquid from said second portion, said tangential filtration means including a bundle of hollow fibers; and
    transverse filtration means disposed in the casing, for conducting the separated second portion in a radial direction in the casing and for biospecifically purifying the second portion of the liquid through flow of said liquid in the radial direction of said casing, said transverse filtration means including a sheet membrane wrapped around said bundle of hollow fibers.

9. A method of biospecifically purifying a liquid containing a portion having cellular elements, the method comprising the steps of:
    tangentially flowing the liquid over a membrane to separate the portion having cellular elements from the portion without cellular elements;
    transversely flowing the portion of liquid without cellular elements through at least one microporous membrane sheet having purifying molecules grafted thereto to remove selected biospecific impurities; and recombining the portion of liquid without cellular elements with the portion of the liquid having cellular elements.

10. An apparatus for biospecifically purifying a liquid having a first portion containing cellular elements and a second portion without cellular elements, the apparatus comprising:

a casing;

means for conducting said liquid into said casing;

means disposed within said casing for tangentially filtering said liquid to separate said first portion from said second portion, said tangential filtering means including a bundle of hollow fibers;

a sheet membrane wrapped around said bundle of hollow fibers for transversely filtering said separated second portion to biospecifically purify the liquid after the separation of said cellular elements; and means for evacuating said first portion and second portion from said casing.

11. An apparatus for biospecifically purifying a liquid having a first portion containing cellular elements and a second portion without cellular elements, the apparatus comprising:

a casing;

means for conducting said liquid into said casing;

a bundle of hollow fibers disposed within said casing for tangentially filtering said liquid to separate said first portion from said second portion;

a sheet membrane wrapped around itself and disposed within said bundle of hollow fibers, for transversely filtering said separated second portion to biospecifically purify the liquid after the separation of said cellular elements; and means for evacuating said first portion and second portion from said casing.

12. A device for biospecifically purifying a liquid having a first portion containing cellular elements and a second portion without cellular elements, said device comprising:

a casing;

means for conducting said liquid into said casing;

means disposed within said casing for tangentially filtering said liquid to separate said first portion from said second portion, said tangential filtering means including an inner bundle of hollow fibers;

means disposed within said casing for transversely filtering said separated second portion to biospecifically purify the liquid after the separation of said cellular elements, said transverse filtering means including an annular bundle of hollow fibers surrounding said inner bundle; and means for evacuating said first portion and second portion from said casing.

13. A device for biospecifically purifying a liquid having a first portion containing cellular elements and a second portion without cellular elements, said device comprising:

a casing;

means for conducting said liquid into said casing;

means disposed within said casing for transversely filtering the second portion of the liquid to biospecifically purify the liquid after separation of said cellular elements, said transverse filtering means including an inner bundle of hollow fibers;

means disposed within said casing for tangentially filtering said liquid to separate said first portion from said second portion, said tangential filtering means including an annular bundle of hollow fibers surrounding said inner bundle; and means for evacuating said first portion and second portion from said casing.

14. An apparatus for biospecifically purifying a liquid having a first portion containing cellular elements and a second portion without cellular elements, the apparatus comprising;

a tubular casing;

inlet means for flowing the liquid in an axial direction in the tubular casing;

tangential filtration means for separating said first portion of the axially flowing liquid from said second portion, said tangential filtration means including a bundle of hollow fibers; and transverse filtration means disposed in the casing, for conducting the separated second portion in a radial direction in the casing and for biospecifically purifying the second portion of the liquid through flow of said liquid in the radial direction of said casing, said transverse filtration means including a sheet membrane wrapped around itself and disposed within said bundle of hollow fibers.

15. An apparatus for biospecifically purifying a liquid having a first portion containing cellular elements and a second portion without cellular elements, the apparatus comprising:

a tubular casing;

inlet means for flowing the liquid in an axial direction in the tubular casing;

tangential filtration means for separating said first portion of the axially flowing liquid from said second portion, said tangential filtration means including an inner bundle of hollow fibers; and transverse filtration means disposed in the casing, for conducting the separated second portion in a radial direction in the casing and for biospecifically purifying the second portion of the liquid through flow of said liquid in the radial direction of said casing, said transverse filtration means including an annular bundle of hollow fibers surrounding said inner bundle.

16. An apparatus for biospecifically purifying a liquid having a first portion containing cellular elements and a second portion without cellular elements, the apparatus comprising:

a tubular casing;

inlet means for flowing the liquid in an axial direction in the tubular casing;

transverse filtration means disposed in the casing, for conducting the second portion of the liquid in a radial direction in the casing and for biospecifically purifying the second portion of the liquid through flow of said liquid in the radial direction of said casing, said transverse filtration means including an inner bundle of hollow fibers; and tangential filtration means for separating said first portion of the axially flowing liquid from said second portion, said tangential filtration means including an annular bundle of hollow fibers surrounding said inner bundle.

* * * * *